United States Patent
Hess

(10) Patent No.: US 6,295,468 B1
(45) Date of Patent: Sep. 25, 2001

(54) APPARATUS FOR MEASURING BIOELECTRICAL PARAMETERS

(76) Inventor: Bruno M. Hess, 14860 Shrike Way, Fort Myers, FL (US) 33908

( * ) Notice: Subject to any disclaimer, the term of this patent is extended or adjusted under 35 U.S.C. 154(b) by 0 days.

(21) Appl. No.: 09/523,430

(22) Filed: Mar. 10, 2000

(30) Foreign Application Priority Data

Mar. 13, 1999 (DE) .............................................. 199 11 200

(51) Int. Cl.[7] .................................................. A61B 5/05
(52) U.S. Cl. ........................................... 600/547; 600/554
(58) Field of Search ..................................... 600/547, 548, 600/554; 128/907; 607/1; 606/32, 34, 35, 41

(56) References Cited

U.S. PATENT DOCUMENTS

| | | | |
|---|---|---|---|
| 3,834,374 | * 9/1974 | Ensanian | 600/397 |
| 3,971,366 | * 7/1976 | Motoyama | 600/384 |
| 4,807,643 | * 2/1989 | Rosier | 600/554 |
| 4,940,060 | * 7/1990 | Gu et al. | 600/548 |
| 5,797,854 | * 8/1998 | Hedgecock | 600/554 |

* cited by examiner

Primary Examiner—Robert L. Nasser
Assistant Examiner—Charles Marmor, II
(74) Attorney, Agent, or Firm—Heslin Rothenberg Farley Mesiti, P.C.

(57) ABSTRACT

An apparatus for measuring biological parameters of the human or animal body at acupuncture points, in particular of a bodily voltage or of an electrical resistance, making use of two constant current sources for the production of two constant currents of equal strength but different polarity. The constant currents are applied via measuring and earthling electrodes to the body. For the determining of an inherent bodily voltage and its resistance the potential differences between measurement and earthed electrodes are measured with a positive and negative constant current. From the two potential differences the bioelectrical strength is then determined.

20 Claims, 8 Drawing Sheets

SIGNS AND SYMBOLS

↑ +8V
⊥ REFERENCE GROUND
↓ −8V

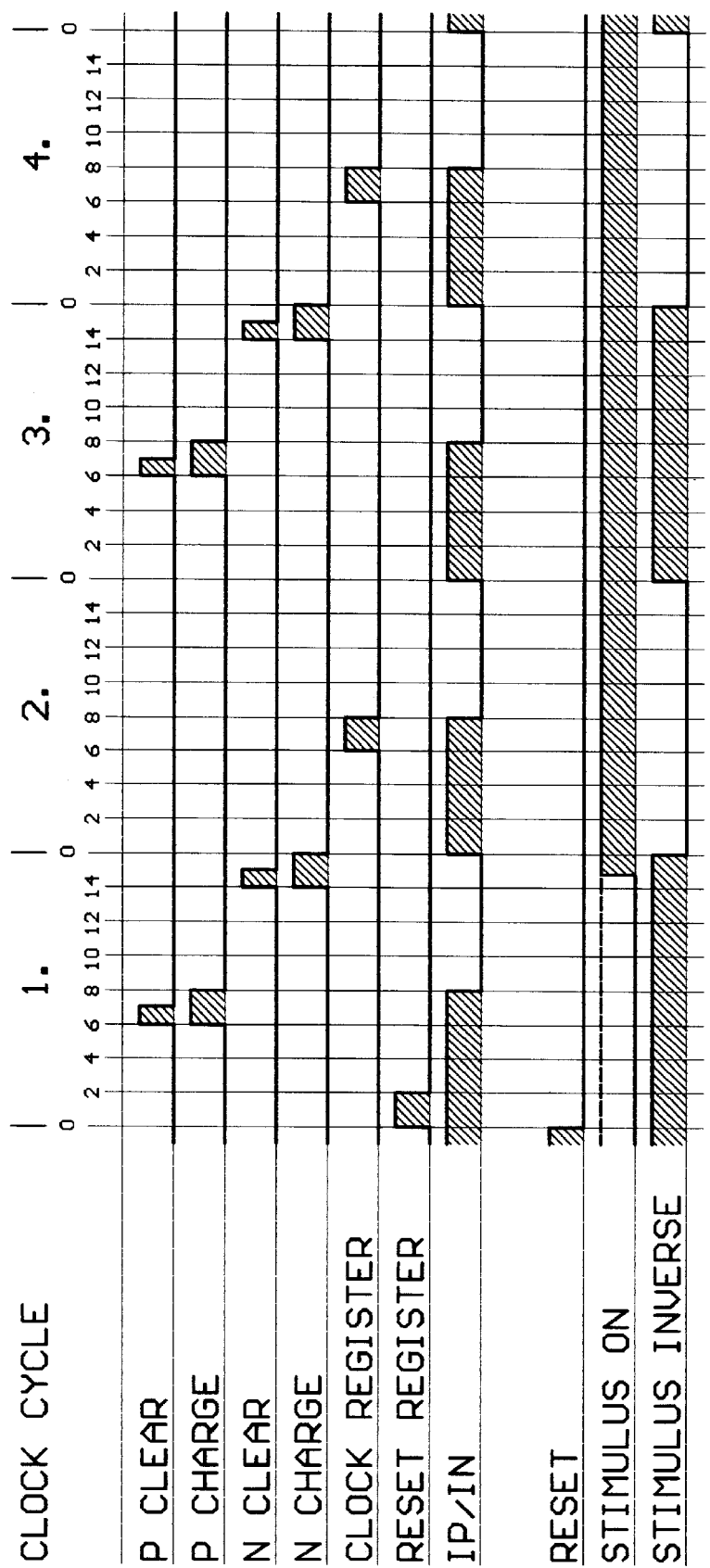

APPARATUS FOR MEASURING BIOELECTRICAL PARAMETERS

FIELD OF INVENTION

The invention relates to an apparatus for measuring bioelectrical parameters of the human or animal body at acupuncture points by the implementation of a bioelectrical function diagnosis.

BACKGROUND INFORMATION

The bioelectrical function diagnosis as an alternative diagnosis method proceeds from the ground rule system, which describes the human body as a control loop that responds to external stimuli. The bioelectrical function diagnosis proceeds from the fact that an external stimulus leads to an interruption in the control loop. This interruption can be demonstrated whenever certain bioelectrical measures change at acupuncture points. With bioelectrical function diagnosis, functional interruptions of individual organs can be inferred from deviations from the regular process described as normal ("The system of a ground rule and bases of a holistic biological medicine, Prof. Dr. med. Alfred Pischinger, Karl F. Haug Publishers, Heidelberg").

Various devices are known for ascertaining potential differences and resistances as biological measures, whereby electrical measures can be read by means of electrodes on the skin surface of the body. It is a matter here of conventional voltage or resistance measuring devices. In practice, it has been shown that values derived from known devices for voltage and resistance can be afflicted by considerable errors of measurement, since they do not deliver the required relative measures in a way that can be reproduced.

Therefore, it is the underlying task of the invention to create an apparatus for measuring bioelectrical values of the human and animal body at acupuncture points that has a high level of accuracy and delivers reproducible measurement values.

BRIEF SUMMARY OF THE INVENTION

The achievement of this task ensues according to the invention with the characteristic of patent claim 1.

The invention-conforming apparatus comprises a measuring electrode for the production of a first electrical skin contact and an earth electrode for the production of a second electrical skin contact. The measuring process is based on a constant electrical current being applied at an acupuncture point that flows from the one to the other electrode. The measuring process proceeds from the fact that the test section in the body between the electrodes can be described very approximately by a simplified electrical equivalent circuit diagram, consisting of the series circuit of a bodily voltage source and an electrical resistor. When a current flows over the test section, measurements are thus taken of the sum of the two voltages, namely the voltage drop at the resistor and the bodily voltage. The voltage at the resistor is found according to Ohm's law from the product of the current over the test section and the value of the resistance ($U = R \cdot I$).

The invention-conforming apparatus now allows the determining of bioelectrical parameters, especially of bodily voltage and/or of the electrical resistance of the test section. Instead of resistance, information can also be gained about conductivity, which is the reciprocal value of resistance.

The potential differences between the measuring and earth electrode are measured when there is a constant current flow from the measuring to the earth electrode and from the earth to the measuring electrode. From both potential differences with a positive and negative constant current, it is possible to determine the bioelectrical measure. The determining of the bioelectrical measures ensues preferably in an analogue or digital calculator by adding the sum of both measured potential differences.

The inventor has acknowledged that too great a current can lead to an exchange effect with the body and so lead to a falsification of the measurement results. It has been shown that reliable measurement results can be attained if the current is <50 nA, preferably <10 nA. More meaningful measurements can only be attained with the known measuring devices if the current is reduced to a value which has no influence on the bioelectrical control loop, independently of whether the bioelectrical measures are determined with positive and negative current.

In a preferred embodiment, the apparatus comprises means of indicating the bioelectrical measures. The bioelectrical measures can for example be shown on digital or analogue indicators. The measurement values can also be stored and electronically evaluated.

The means for producing the positive and negative constant current include more advantageously two constant current sources and a switch-box, which alternately switches one current source on and the other off. To be able to produce two constant currents of the same value but with different polarity, it is more advantageous to construct the constant current sources in a complementary way. This reduces measurement inaccuracies based on temperature changes.

In a further preferred embodiment, both constant current sources produce a current greater than the measurement current. This current then serves to produce the actual measuring current. It is more advantageous here to supply a voltage-sequential switched operational amplifier. This has the advantage of thereby simplifying the switching technological design of the constant current source.

In a preferred configuration, means are supplied to eliminate interruptions that can lead to a considerable falsification of the measurement results.

The means to eliminate interruptions for example from the main supply can include a filter at the outlet of the operational amplifier, having at least one R/C link.

Assuming that the overlapping interrupted voltage of the direct current is an alternating current with a symmetrical course, a particularly effective elimination of the interspersions can be attained by getting an average of the peak values of the first and second potential difference. In the case of a symmetrically curved form of the interrupted voltage, the average corresponds exactly to the direct current. More meaningful measurement results can be gained from known measuring devices only with such elimination of disturbances, independently of whether the measurements are read with a positive or negative constant current.

The earth electrode is preferably a surface electrode, for example, in the form of an adhesive band attached to the wrist, while the measurement electrode is preferably in the form of a touch electrode applied under slight pressure to the skin at the respective acupuncture point.

Furthermore, the inventor has acknowledged that electrodes made of metal can lead to a falsification of the measurement results. The measuring and/or earth electrode are therefore preferably carbon electrodes. Synthetically bound carbon fibres have proved particularly advantageous. Using carbon electrode reduces interactions with the body through electrolytic processes.

In order to evaluate the measurement results in a personal computer, there are provided means for the digitalizing of measurement values and an interface as an attachment to the PC, which for example permit the designation of measurement curves, or the like. The analog/digital adaptor can be made available as a separate unit, whereby the analog values are given out via the interface. Preferably, the interface would be a serial or parallel interface for the transfer of digitalized signals, for example, a Centronics interface.

The invention-conforming apparatus can show one or a number of measure-points which preferably can be consulted in turn via a measure-point commutator, for example, a multiplexer.

BRIEF DESCRIPTION OF THE SEVERAL VIEWS OF THE DRAWINGS

In the following, a working example of the invention is explained in relation to the drawings.
They show:

FIG. 9 a time-cycle diagram of the circuit of FIGS. 1 to 8.

DETAILED DESCRIPTION

Figure 1:
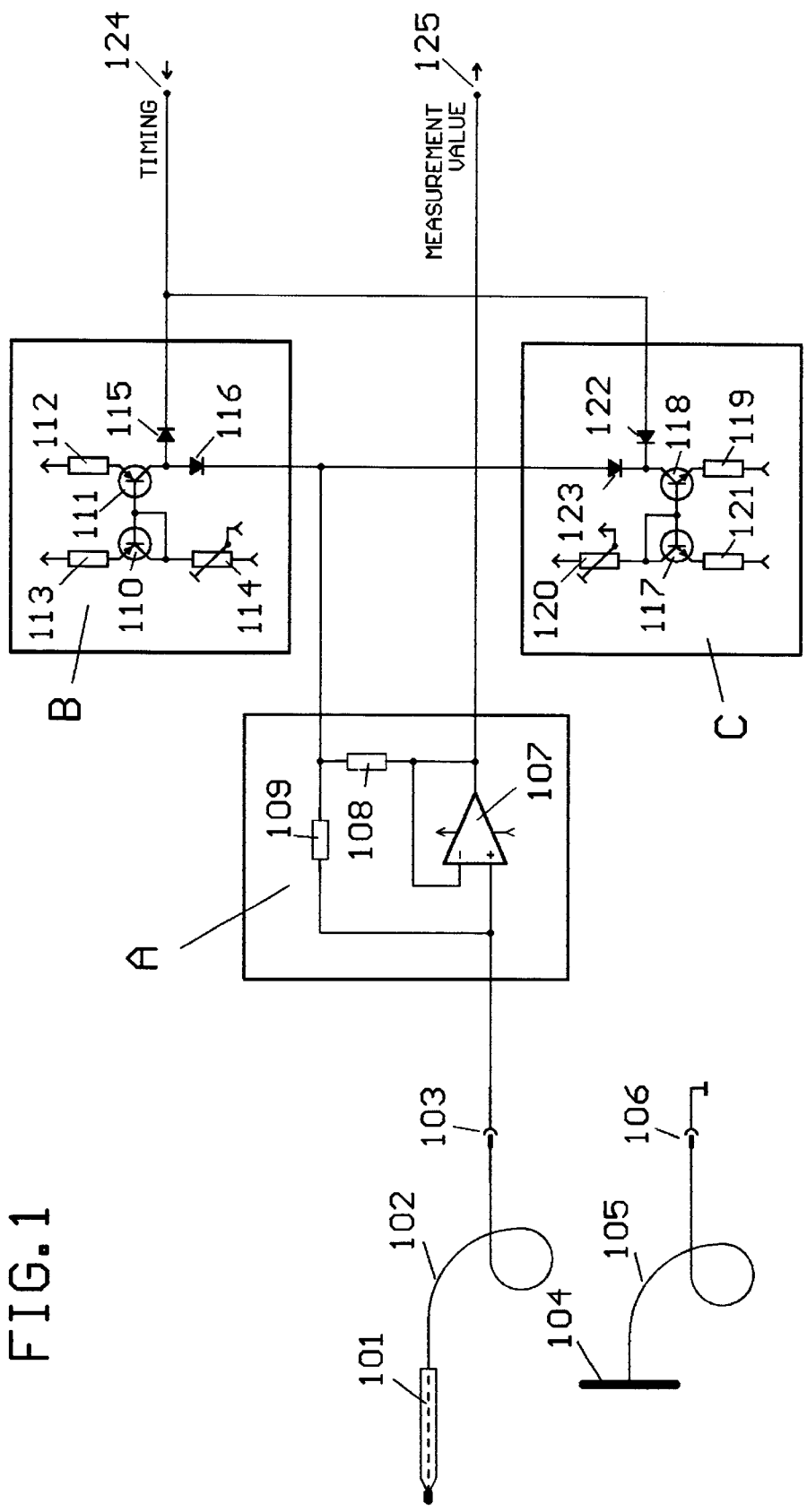
FIG. 1 a first view of the switching arrangement of the invention-conforming apparatus in which the circuit components are represented for the pick-up of measurement values, FIG. 2 a second view of the switching arrangement in which the circuit components for the determining of the bioelectric parameters from the measurement values are represented, FIG. 3 a third view of the switching arrangement, in which the clock signal generator is represented.
Figure 2:
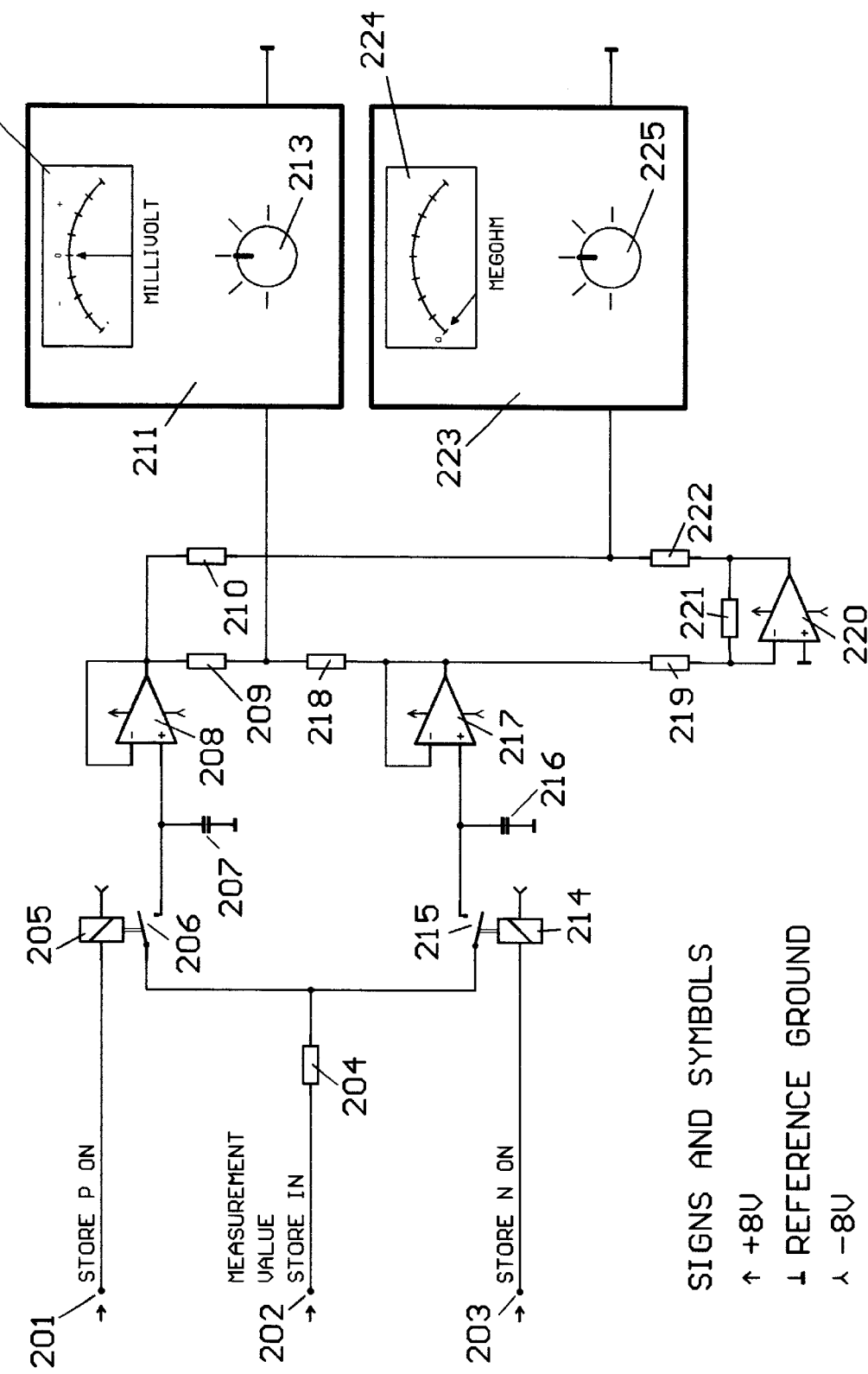
Figure 3:
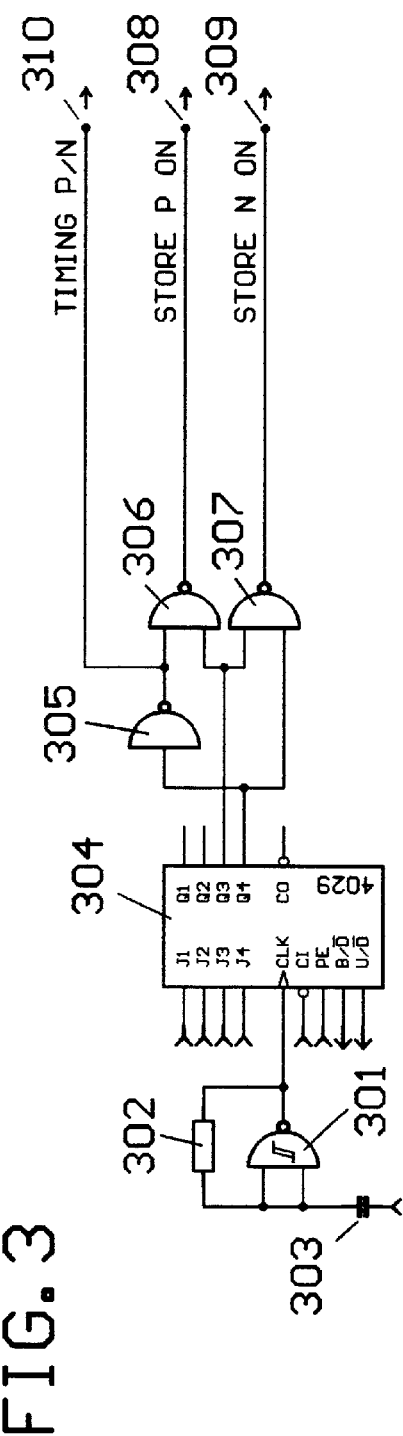

The FIGS. 1 to 3 show the principle circuit of the apparatus for measuring bioelectrical parameters whereby all additional wiring, e.g. the offset alignment and the measurement range changeover switch are familiar to the expert have been left out because they are clear.

FIG. 1 shows the part of the circuit for pick-up of the measurement values. For the production of skin contact a measuring electrode 101 and an earth electrode 104 have been provided from synthetically bound carbon fibres. The measuring electrode 101 which is a touch electrode has bound carbon fibres after the fashion of a paint brush which are impregnated with epoxy resin, while the earth electrode 104 in the form of a surface-electrode is a correspondingly produced band.

The surface electrode 104 is linked via the connecting lead 105 and the plug connection 106 to the earth device, i.e. the reference potential for measurement. The touch electrode 101 is connected via lead 102 and the plug connection 103 with the non-inverting input of the operational amplifier 107, where the output of the operational amplifier is connected via a series circuit of two resistors 108,109 with its inverting input.

The operational amplifier 107 possesses FET-inputs, whose input resistors lie in the giga ohm range and represent practically no current load. The counter-coupling of the output of the operational amplifier 107 to the negative input is a direct connection. In this way the operational amplifier 107 functions as a pure current amplifier where it can be calculated as one with the voltage amplification. A voltage amplification is not required in this case because the modulation range amounts to only approx. +/−5 volts, which is exactly enough to make available the service signal with the overlapping interruption signal from the main supply caused through wiring in the walls and ceilings as undistorted measurement value at connection point 125.

The measurement amplifier A forms together with the constant current source B and the negative constant current source C the measurement value pick-up to whose inlet 103 a constant flow of a few nano amperes is supplied via resistor 109, alternately timed, positive/negative, with exactly similar strength of current and timing. This constant current flows over the test section, so long as the voltage drop at its resistor plus its own voltage lies within the range +/−5 volts. This technique of circuitry of the constant current is produced by the positive timed phase supplied via attachment 124 blocking the negative constant current source C via diode 122 and freeing the constant current source B at diode 115. A positive current flows through this whose strength is set more advantageously at an easily controlled value of some 1 milliampere, via the resistor 108 to the low ohm output of the operational amplifier 107 and produces at the resistor 108 a voltage drop which in this embodiment is 400 millivolts more positive than the measurement value. As the output of the operational amplifier 107, i.e. the measurement value always follows the input voltage, there is also a constant voltage at resistor 109 that is 400 millivolts more positive than the input voltage, on account of which there is a constant current, independently of the voltage at the input. The resistance value determines its strength and in this case amounts to 40 megaohms, from which a current of 10 amperes results in I=U/R. The input and therefore also the output voltage is the sum of the inherent voltage of the test section and of the voltage drop at its resistor. During the negative time phase, the positive current source B is switched off and the negative constant current source C switched on. The previously described way of working is the same but the other way round. Simple transistor circuits serve as constant current sources. The base of the PNP transistor 111 is linked with the base and the collector of the transistor 110 of the same type, which together with the resistor 113 and the trimmer resistor 114 forms a voltage divider and is so proportioned that approx. 1 volt drops at resistor 113. The transistor 110 serves as temperature compensator of transistor 111, which works best when both transistors work roughly at the same work-point, on account of which resistor 112 has the same resistance value. The current requirement in this case is only of subsidiary importance, as a constant flow of 0.5 to 1 milliampere is sufficient.

The transistor 111 regulates in operating condition its collector current in such a way that the voltage drop at emitter resistor 112 corresponds to the constant voltage drop at resistor 113. The emitter current is collector current plus base current, the base current however produces less than 1%, changes only in non-essentials and is discounted. The constant current so achieved is supplied via diode 116 to the measurement amplifier A, as already described. The negative time-phase at diode 115, as also described, shunts the positive constant current. Diode 116 here prevents a back-flow from the measurement amplifier. The negative time signal releases the balanced negative constant current C at diode 122, which along with NPN transistors 117 and 118, the trimmer resistor 120, the emitter resistors 119 and 121, as well as the diode 123 send a negative constant current during the negative time phase to the measurement amplifier A. With trimmer resistors 114 and 120, the strength and balance of the constant currents and thus of the measurement current can be adjusted exactly.

The input resistor of the measurement circuit lies within the measurement range and in operating condition in the giga ohm range, an unavoidable precondition for the measurement process, although the resistor 109 in this embodiment shows only 40 mega ohms. This resistor is only effectively practicable with a non-linearity of the constant current sources. An assumed non-linearity of 1% means, e.g. that the current path via this resistor with 40 mega ohms in normal functioning corresponds to a parallel earthed resistor of 4 giga ohms.

This measurement circuit delivers as measurement value a voltage which is composed of the sum of inherent voltage of the test section and the voltage drop resulting from the supplied constant current. The sum of the inherent voltages of the test section is adopted as the bioelectrical parameters to be determined, namely the bodily voltage. In order to obtain a parameter that is meaningful for evaluation, the separation of the sum of inherent voltages and voltage drop in the test section is required.

To separate the voltages, it is necessary for the measurement value to come from a non-polar constant current which moreover reduces the problem of electrolysis that exists despite the use of neutral carbon electrodes. The output of the measurement value pick-up 125 gives alternately a time-phased value respectively, which is set to a positive or negative constant current supply.

Figure 4:
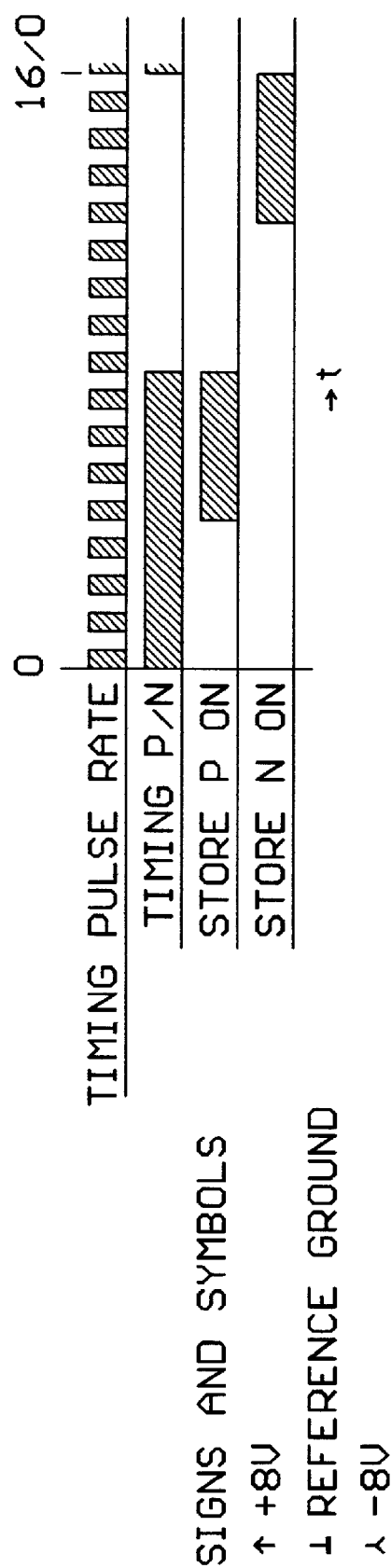
FIG. 4 a cycle time diagram of the circuit of FIGS. 1 to 3.

FIG. 3 shows the clock signal generator designed with standard ICs with the generally known C-MOS-series 40XX. The inverse output of the trigger 301 is linked to the CLK input of the four-position binary counter 304 and via the feedback resistor 302 with the parallel switching inputs and the capacitor 303, whose second attachment lies at the negative potential of the stabilised power voltage. In this way the trigger element 301 switched as non-stable multivibrator and the binary counter 304 constantly moves round, i.e. the key 16 is equivalent to 0. The output Q4 of the binary counter 304 is linked to the input of the NAND—element 307 and the input of the invert 305, whose output is connected with an input of the NAND element 306 and gives directly the timing P/N 310 which controls the measurement value pick-up at time input 124. The output Q3 of the binary counter 304 is linked to the second inputs of NANDS 306 and 307. The NAND-element 306 delivers at output 308 the timing "Store P in" and the NAND-element 307 at outlet 309 the timing "Store N in". The timing sequence is 0.5 Hz. The time-phase scheme also shown in FIG. 4 illustrates the chronological succession of the timing.

FIG. 2 shows the part of the circuit for the evaluation of the measurement values. The measurement value output 125 of FIG. 1 is linked with the measurement value input 202 of FIG. 2. There are two relays present, preferably reed-relays, 205 and 214, which divide the measurement value time controlled with a positive and negative current. The coil terminal 201 of relay 205 is linked with the timing output 308 (FIG. 3) The coil terminal 203 of the relay 214 is linked with timer output 309 (FIG. 3). During the positive time-phase, the set measure value stands at a positive constant current. Within this time span the relay 205 is actuated, whereupon contact 206 shuts off and the connection of measurement value input 202 via resistor 204 to the condensor 207 is created. Condensor 207 is thereby charged with the voltage potential of the measurement value. At the end of the positive timing phase relay 205 cuts out, contact 206 opens up and the voltage potential of the positive measurement value is retained as condensor charge. In the same way, the negative measurement value is fed via resistor 204 and contact 215 to condenser 216, which stores the voltage potential of the negative measurement value. Instead of reed-relays, electronic CMOS switches can also be installed. The store condensers 207 and 216 are respectively connected to the non-inverting inputs of the operational amplifiers 208 and 217, whose outputs are linked directly with the inverting inputs. It is preferable to use operational amplifiers with high ohm FET inputs so that the charged voltage potential in condensors 207 and 216 is optimally retained and is available at their outputs for stable and loadable re-use. The inherent voltage and polarity of the test section compared with the earth potential reference potential is indicated by millivoltmeter 212 on its scale 211 as zero in the middle, which is linked on the one side to the earth potential and on the other side to the resistors 209 and 218. The other side of the resistors is linked with the outputs of the operational amplifier 208 or 217.

As the voltage drop at the resistor of the test section caused by the constant current, independently of the sum of its inherent voltages, both with positive and negative current, possesses the same strength, but the other way round, this part of the measured value is mutually cancelled, and against the reference potential earth there remains only the sum of inherent voltages within the test section, i.e. bodily voltage, which is shown by measurement instrument 211. The voltage to be indicated, in a few exceptional cases, lies somewhat higher than −1000 millivolts, most frequently between −100 and −300 millivolts, although positive values can also occur on account of which a measurement range commutation 213 is present.

The resistance of the test section is shown by measuring instrument 223, also a millivolt meter with a range commutation 225, whose scale 224 is calibrated in mega ohms and has the zero at the left end of the scale, as the electrical resistance shows no polarity. Which polarity the voltage to be indicated against the reference potential earth should have is determined by the switch design, and in the present case the polarity is basically positive, which is fixed by inverting the negative measurement value. For this purpose, there is an operational amplifier 220, whose inverting input is connected via resistor 219 with the output of operational amplifier 217 and via resistor 221, showing the same resistance value, to its own output. Here too, the equal-value resistors 222 and 210 form a voltage divider between the outputs of operational amplifiers 220 and 208, to whose middle, pick-off measuring instrument 223 is attached. This too, as an ohm meter with a measuring instrument calibrated on a linear scale is linked on the other side with the earth reference potential.

Here the inverting of the measurement value with negative constant current has the effect that it works the other way round, i.e. the sum of the inherent voltages of the test section accepts the reversal and cancels itself out, while the part of the voltage caused within the test section by the resistor also becomes positive and stands at the middle pick-off of the voltage divider opposite the reference potential earth, formed from resistors 210 and 222.

Resistor 204 and condenser 207 or 216 form a R/C component whose time constant can be selected in such a way that interruptions from the mains supply arising from the wiring in walls and ceiling are filtered out sufficiently for an adequate measurement accuracy to be achieved. The consequence of this is however that a very long period, for instance 20 seconds, can take place. In order to eliminate interruption influences, it is possible to provide screening or the like.

The example of the embodiment with reference to the figures shows only one measurement position. The apparatus for measuring bioelectrical parameters can however have available several measurement positions, with which the regulation processes at various acupuncture points can be simultaneously checked.

The regulation test with the apparatus for measuring bioelectrical parameters can be carried out, for example, as follows. First, the surface electrode 104 is attached to the wrist and the touch electrode 101 is applied with slight pressure to an acupuncture point. Then the bodily voltage and the resistance are measured as basic values. After ascertaining the basic value, the body is exposed to a stimulus. Preferably, this occurs through a stimulus current of a few seconds in an order of strength of a few milliamperes. For this a corresponding current source can be provided in the apparatus that is linked with the touch electrode. The reaction of the body to the stimulus current can be ascertained and observed by measuring the bodily voltage and resistance. The bioelectrical function diagnosis proceeds on the basis that the bioelectrical parameters as reaction to the stimulus current change, so that it is possible from a change in the parameters to deduce a malfunction of an organ allocated to the acupuncture point. With the invention-conforming apparatus, the parameters described as reaction value and regulation value can be determined.

A more expensive embodiment that is more suited to practical application is shown in FIGS. 5 to 9. The interval before the measurement result is visible can be essentially shortened, justifying the greater expense. Furthermore, there is a description of the possibility of supplying an additional "stimulus" current. The evaluation for diagnostic purposes of a series of measurements through intermediate interruptions of one's bioelectrical condition can be executed very well and simply by an electrical current, especially as the customary insertion of an acupuncture needle is often painful and hardly capable of administration in doses. In principle, this circuit arrangement contains the same basic elements as the already described simplest embodiment. The 500 series reference number of FIG. 5 which correspond to the 100 series reference numbers of FIG. 1, identify similar components which perform similar functions.

Figure 5:
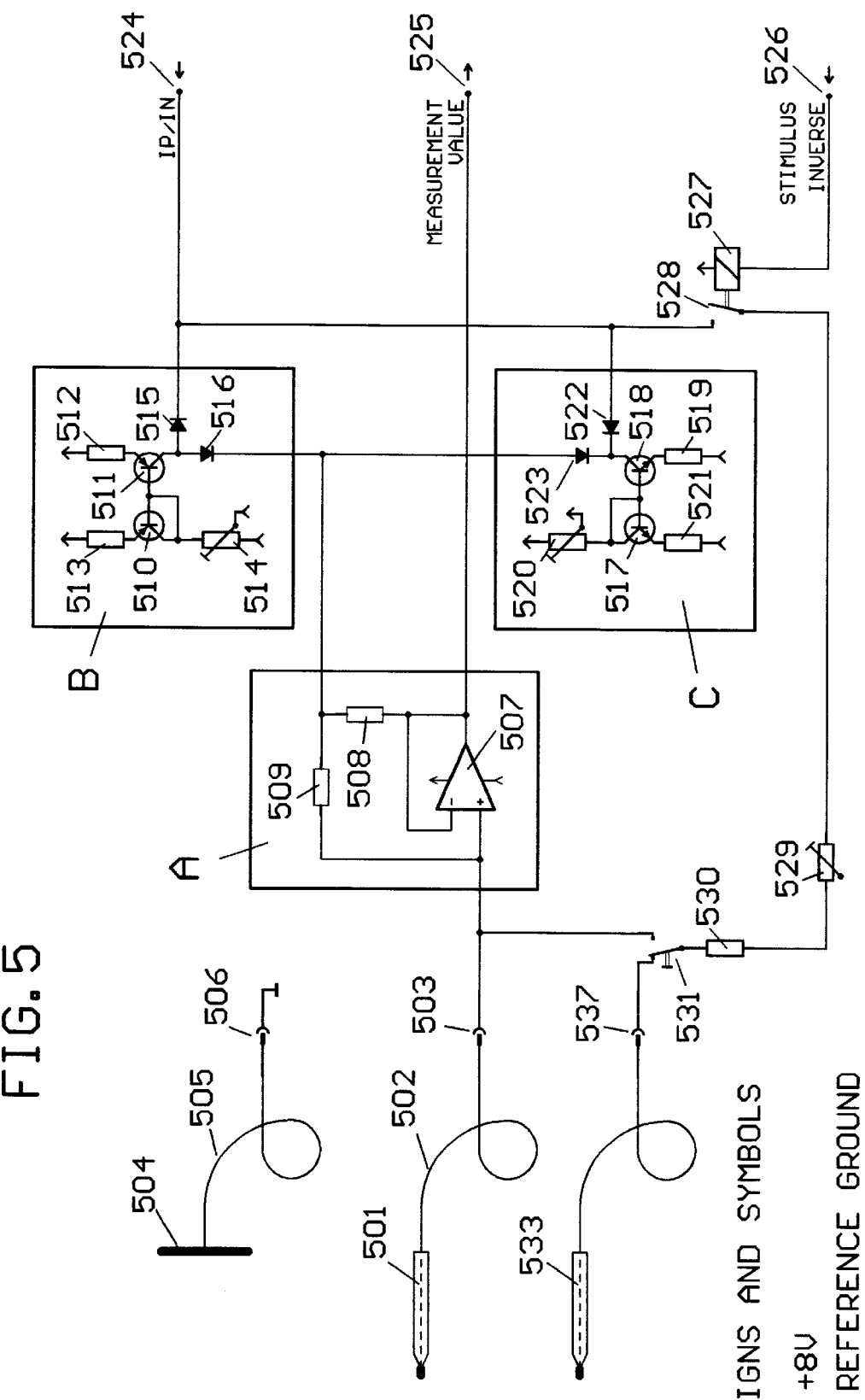
FIG. 5 a first view of the circuit of a further embodiment example of the invention-conforming apparatus in which the circuit components for the pick-up of measurement values and the production of a stimulus current are represented.

The measured value pick-up as in FIG. 1 has been taken over unchanged in FIG. 5. The difference consists merely in drawing in extra elements for the supply of a stimulus current. The fault-clearing, temporary storage and interpretation of measurement values in FIG. 2 is represented in changed form in FIG. 6, where, for the purpose of simpler description and supervision, reference is made to two similar circuits in FIG. 7 and their description. For the control of cooperation there is in service an elaborated clock signal generator (FIG. 8) with an additional switching, to simplify application in practice.

Figure 7:
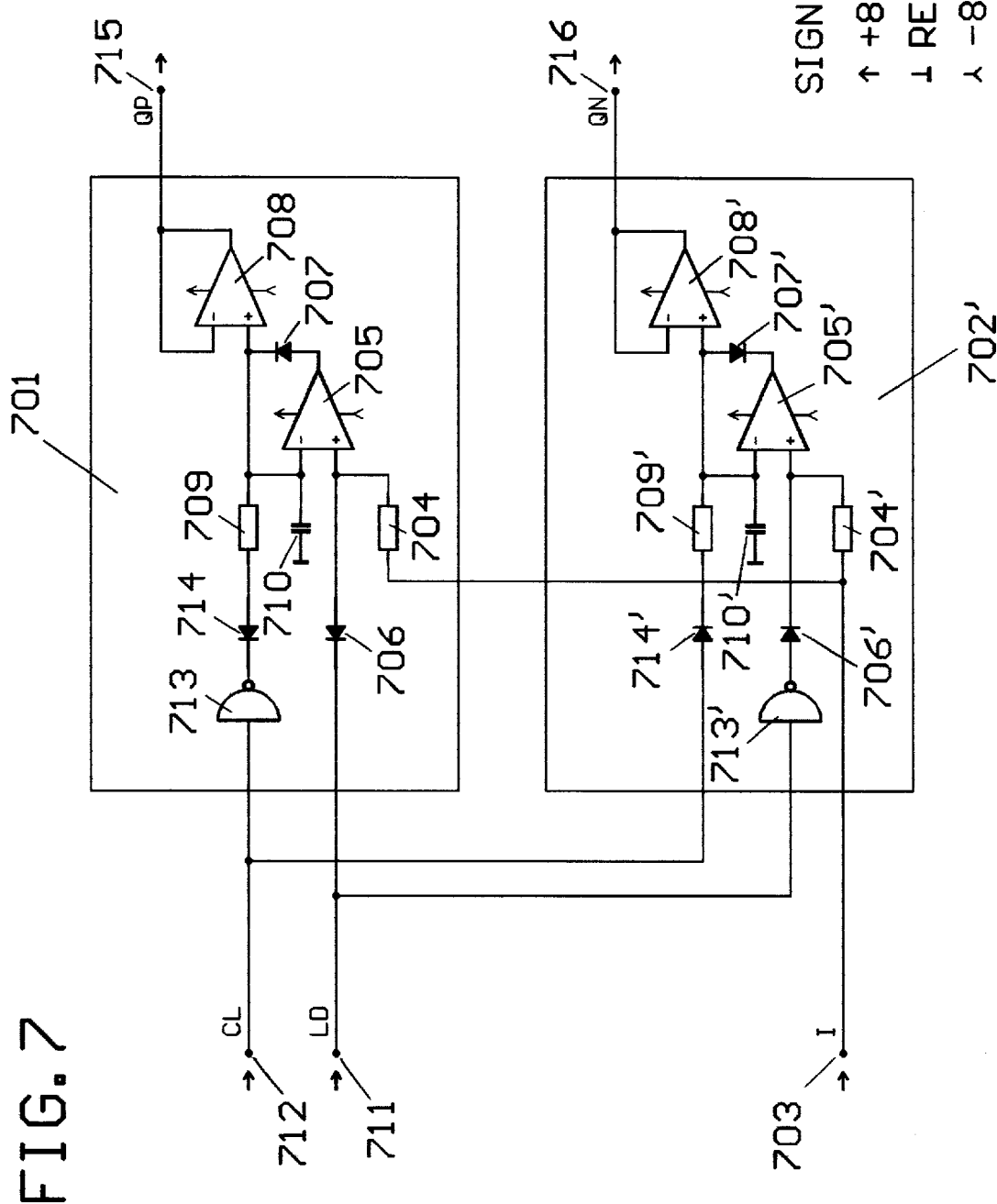
FIG. 7 a peak value store of the circuit of FIG. 6.

FIG. 7 shows two similar but complementary designs of circuits for storage of the positive and negative peak values of the alternating voltage overlapping measurement value. The circuit 701 serves as storage for the positive, circuit 702' for the storage of the negative peak value. The measured value, attachment 703 (I), is supplied via resistor 704 to the non-inverting input of the operational amplifier 705, whose output is linked via diode 707 with its own inverting input, as well as the non-inverting input of operational amplifier 708, resistor 709 and condenser 710. Condensor 710 is linked on the other side with the earth potential and serves as analog value store that can obtain only a positive charge via diode 707, with back-flow on this route being blocked. It is only possible to bring in a negative charge with a positive potential at attachment 712 (CL), linked with the input of inverter 713, whose output in this case is negative, and is wired via the reverse poled diode 714 to its minus pole the other side of resistor 709. Bringing in a positive charge, following the measured value, is on the other hand only possible when there stands positive potential at attachment 711 (LD), which is linked via diode 706 with the non-inverting input of operational amplifier 705. The operational amplifiers possess very high ohm FET inputs, so that the condenser charge is retained during storage time with sufficient accuracy (max. a few seconds). Equally important is the installation of diodes with the least possible residue currents. The operational amplifier 708, whose output is linked to its own inverting input and the attachment 715 (QP), delivers positive peak voltage which was reached during the controlled charge time, with voltage amplification 1, loadable, without any reverse effect on the store condensor 710. It is noteworthy that with this circuitry there is no sign of leak voltage of diode 707. The outlet voltage is practically the same as the actual peak voltage during charge time, apart from the sum of the offset voltages of the operational amplifiers, which are however eliminated as constants with a zero balance.

The complementary circuit 702' similarly stores the negative peak value. To help supervision, the components corresponding to each other are provided with corresponding reference symbols. Of otherwise identical design, the diodes 706', 714', and 707' are reverse-poled. As consequently the switch-off and switch-on signal are fitted the other way round it is not the switch-off but the switch-on signal that has to be inverted. The negative peak value is available at output attachment 716 (QN).

Figure 8:
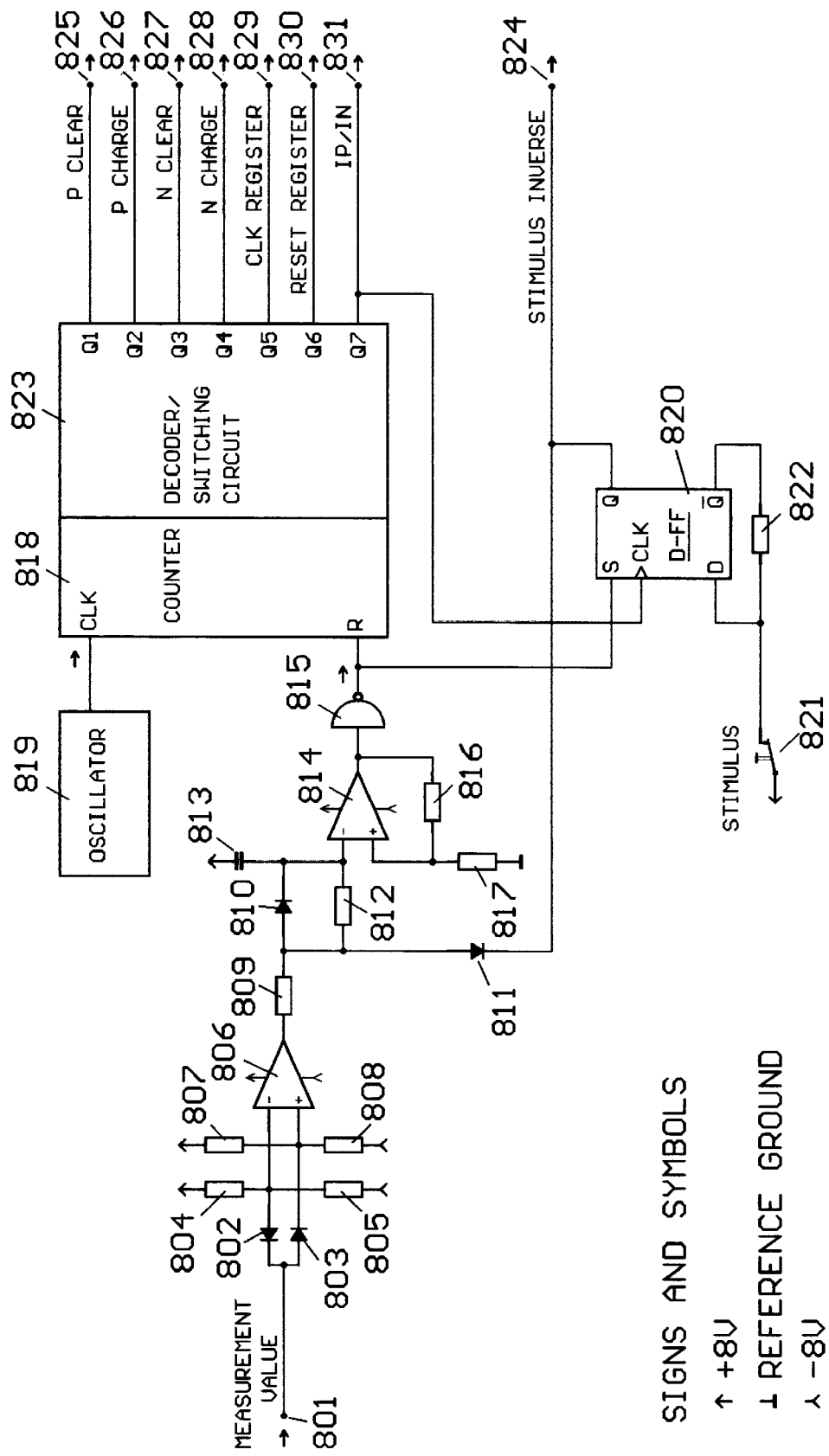
FIG. 8 a third view of the switching arrangement of FIG. 5, in which the clock signal generator is represented.

FIG. 8 contains an extra switching that has proved itself in test installation and has the effect that the measurement result remains indicated after a measuring and automatically cuts out at the start of a new measuring, so that the standing new measurement value is visible. The automatic recognition that a new measure is beginning rests on the fact that on exceeding the control level range, the time cycle counter is set back and maintained, so that the standing value is retained on the indicator. The P/N timing is always kept standing at the set beginning of the 1st timing cycle and starts as soon as the measurement value comes within the indicator range after the touch electrode is attached. A switch to switch-on of the stimulus current as well as the elaborated clock signal generator is also contained.

The measurement value output 525 (FIG. 5) is linked with the input 801 (FIG. 8) and here with the plus pole of diode 802 and the minus pole of diode 803. The minus pole of diode 802 is connected to resistor 804 that is located on the other side at the plus potential of the supply voltage and the inverting input of comparator 806. The plus pole of diode 803 is connected with resistor 807 that is located on the other side at the plus potential of the supply voltage, resistor 808, which is located on the other side at the minus potential of the supply voltage resistor 805, and the non-inverting input of comparator 806. The output of the comparator 806 is linked via the current limiting resistor 809 with the minus pole of diodes 810 and 811 and the resistor 812. On the other side, resistor 812 is connected to the plus pole of diode 810, the inverting input of comparator 814 and the condensor 813, which is located at the other side at the plus potential of the supply voltage. The output of comparator 814 is linked with the inverter 815 and resistor 816, whose other side is connected via the non-inverting input of comparartor 814 and resistor 817, located on the other side at the earth potential. The output of inverter 815 is linked with the S-input (SET) of the D-flipflop 820 and the R-input (RESET) of the timing cycle counter 818, whose CLK input is connected with the output of oscillator 819. The stimulus circuit occurs through the opening up of switch 821, whose one side is linked with the positive potential of the supply voltage and whose other side to the D-input of the D-flipflop 820 and the resistor 822, that is attached on the other side to its inverse output. At output 831 (IP/IN) of the clock signal generator 818/823, there is attached the CLK input of the D-FF 820. The output of the D-FF 820 is connected with the plus pole of diode 811 and the output attachment 824 (INVERSE STIMULUS).

The voltage divider at the inverted input of comparator 806 is so proportioned that a voltage potential approaching the positive modulation range accentuates to a more positive potential via diode 803 and its non-inverting input, so that the output gives a positive signal. The same thing happens if the measurement value becomes too negative as a result of the voltage divider being correspondingly proportioned at the non-inverting input. Through the relatively low ohm resistor 809 that serves only as a current limiter and diode 810, the condensor 813 along with the inverting input of the comparator 814 are very quickly brought to a high positive potential, so that the output is negative. Once inverted by the inverter 815, the positive RESET signal is produced that brings the time cycle counter 818 and the D-FF 820 to the start position and holds it there. With the aid of resistors 816 and 817, the comparator 814 maintains trigger procedure with a large hysteresis range. The charge reversal of condenser 813 to the backflip point occurs via the high ohm resistor 812 more slowly than the duration of a main frequency period. The RESET status thus is maintained so long as the leak voltage of the main frequency interspersion approaches the modulation range, so as to avoid defective measurements. If the measurement value however remains within the modulation range, the reset signal is cancelled and the measurement process begins.

The timing diagram of FIG. 9 shows the chronological position of the timings and their duration. For the stimulus current there is required a greater current strength than for measurement, which with reference to application lies between 50 nano amperes and 2 micro amperes and in the range above 200 nano amperes is more appropriately sent not through raising the measurement current but by the addition of a separate stimulus phase during which no measurement occurs The measurement phase and stimulus phase alternate rather from time cycle to time cycle while the indicated value is static. The stimulus phase can be switched on and off every time during measurement or pre-selected. In this case too measurement begins automatically with a measurement phase (timing diagram 9) so as to make the status value recognizable. When the switch 821 (FIG. 8) is opened up before the start of measurement or before the end of the first time cycle, D-FF 820 flips with every positive edge of the IP/IN time to the other state, and the signal INVERSE STIMULUS arises which controls stimulus phase and measurement phase alternately. The measurement range can be exceeded during the stimulus phase which should however not lead to a switch-off of the measurement. Diode 811 therefore maintains the potential at resistor 812 negative during the stimulus phase.

Figure 6:
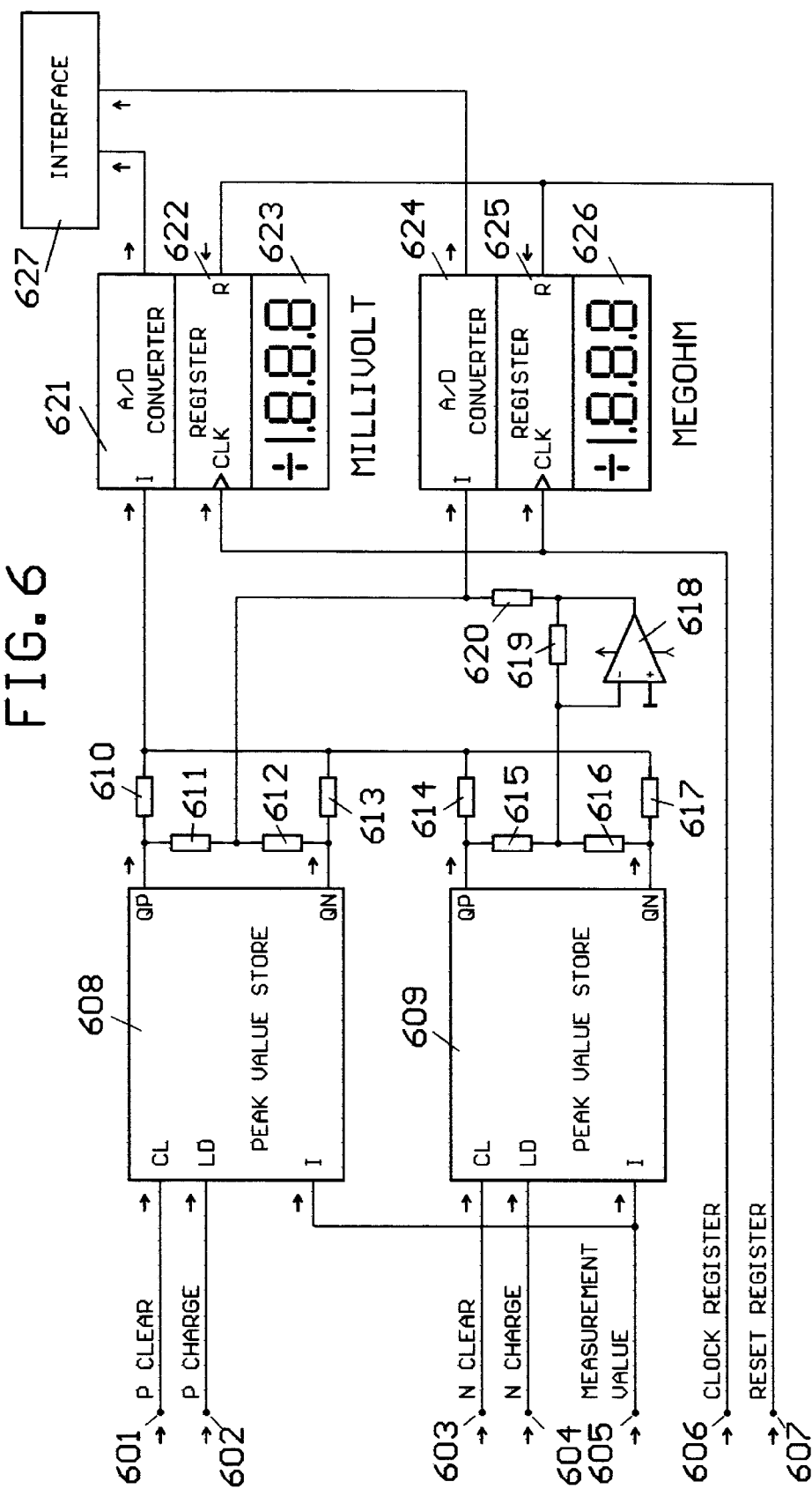
FIG. 6 a second view of the switching arrangement of FIG. 5 in which the circuit components for determining bioelectrical parameters from the measured values through storage of peak and average values are represented.

FIG. 6 shows the measurement value interpretation with interruptions eliminated and the measurement value indications. As a blocking circuit there are illustrated two similar peak value stores, as well as familiar analog digital converters, digital value stores and 7-segment indicators. The analog operational measurement value interpretation corresponds in principle to the circuitry of FIG. 2, with the difference that the mean value is gained respectively from the analog temporary store measurement values. As the inherent voltage of the test section in any case is gained from the mean value of the measurement with positive and negative constant current, the sought-for value can be gained simply through equivalent parallel switched precision resistors and conducted to the analog-digital converter. To ascertain the resistance value however, the mean value is firstly gained from the positive and negative peak voltage, since one of the measurement values is to be inverted. The A/D convertors run constantly alongside, their values are taken up at the appropriate valid point in time with the edge of the phase "CLK STORE" into the digital store decoded and shown on the indicator. The RESET signal only has the purpose that, in the event of a measurement attempt with incomplete measurement phase no defective indications are interpreted, i.e. the old value continues to stand.

The measurement value of the output attachment 525 (FIG. 5) is sent via the input attachment 605 to the inputs I of the peak value store 608 and 609. The timing "P-OFF" of the clock signal generator (FIG. 8) output attachment 825, is connected with the input attachment 601 and further with the input CL of the peak value store 608. In the same way, the timing "P-ON" of output attachment 826 (FIG. 8) is connected with the input attachment 602 and further with input LD of the peak value store 808. The timing "N-OFF" of the clock signal generator, (FIG. 8), output attachment 827, is linked to input attachment 603 and further with input CL of peak value store 609. In the same way, the timing "N-ON" of output attachment 828, FIG. 8, is linked to input attachment 604 and further with the input LD of peak value store 609. The output QP of peak value store 608 is connected with resistors 610 and 611, the output QN, with resistors 612 and 613. The output QP of peak value store 609 is linked to resistors 614 and 615, the output QN to 616 and 617. The other side of the resistors 610, 613, 614 and 617 is connected to the input I of the A/D converter 621. The other side of resistors 615 and 616 is linked to the inverting input of the operational amplifier 618 and the resistor 619, whose other side is connected to the output of operational amplifier 618 and resistor 620. The other side of the resistors 611, 612, and 620 is linked to the input I of the A/D converter 624. The data outputs of the A/D converter 624 are directly connected with the data inputs of the digital store 625 and whose data outputs directly with the internal decoders of the digital indicators 626. The data outputs of the A/D converter 621 are directly linked with the data inputs of digital store 622 and whose data outputs directly with the internal decoder of the digital indicators 623. The timing "CLK STORE" output attachment 829, FIG. 8, is connected with the input attachment 606 and further with the CLK inputs of both digital stores 622 and 625. The output attachment 830, FIG. 8, "RESET" is linked to input connexion 607 and again with the R-inputs of digital stores 622 and 625. For the display of measurement values on a personal computer, there is provided also a Centronics interface 627, that is connected via data-links with the A/D converters 621, 624.

FIG. 5 shows the circuitry of the measurement value pick-up of FIG. 1 unchanged, whose description here is also valid. There is illustrated just one additional wiring for the conducting of a stimulus current that is mentioned (FIG. 8) in the description of the timing control. With the timing "STIMULUS INVERSE" a reed-relay switches the timing "IP/IN" via an adjustable resistor and via a fixed resistor for the limiting of the maximum current directly to the measurement electrode or reversibly on to a second touch electrode. For an adjustable resistor it is better to use a decimal resistor for improved reproducibility.

The reed-relay 527 is attached on the one side to the plus potential of the supply voltage and on the other side via the input attachment 526 at the output attachment 824 (FIG. 8, STIMULUS INVERSE) of the timing control. The relay contact 528 is attached on the one side to the input attachment 524 (TIMING IP/IN) and on the other side to the regulator resistor 529 whose other side is attached to the fixed resistor 530. The other side of the fixed resistor is linked to the base contact of the change-over switch 531, whose closed circuit contact is connected via the plug connector 537 with stimulus electrode 533. The operational contact of the change-over switch 531 is linked to the plug-connector 503, leading to touch electrode 501.

What is claimed is:

1. Apparatus for measuring of bioelectrical parameters of a human or animal body at acupuncture points, said bioelectrical parameters including bodily voltage or electrical resistance, comprising:

a measurement electrode for production of an electrical skin contact and an earth electrode for production of a second electrical skin contact, means for producing a positive constant current which flows by attached electrodes from the measurement electrode over the body to the earth electrode, and a negative constant current which flows from the earth electrode to the measurement electrode, means for ascertaining of a first potential difference between the measurement electrode and the earth electrode, when a positive current flows, and a second potential difference between the measurement electrode and the earth electrode, when a negative constant current flows, and means for determining of bioelectrical parameters from the ascertained first and second potential difference.

2. Apparatus according to claim 1, wherein the negative and positive constant is <50 nA.

3. Apparatus according to claim 2, wherein the negative and positive constant current is <10 nA.

4. Apparatus according to claim 1, wherein the means for determining of bioelectrical parameters include means for finding a sum of the first and second potential difference.

5. Apparatus according to claim 1 further comprising means for indicating the bodily voltage or resistance or conductibility.

6. Apparatus according to claim 1, wherein the means for producing a positive and negative constant current include first and second constant current sources and a switching device that alternately switches one constant current source on and one off.

7. Apparatus according to claim 6, wherein the first and second constant current sources are designed to be complementary.

8. Apparatus according to claim 1, wherein the means for producing a positive and negative constant current comprises an operational amplifier wired as a voltage sequencer with an inverting input and a non-inverting input and an output, where the output of the operational amplifier is linked via a series circuit of a first and second resistor with the non-inverting input and the measurement electrode is linked with the non-inverting input, and the positive and negative constant current is fed into a connection point between the resistors.

9. Apparatus according to claim 8, wherein means are provided for elimination of interruptions.

10. Apparatus according to claim 9, wherein the means for elimination of interruptions include a filter at the output of the operational amplifier having at least one R/C component.

11. Apparatus according to claim 9, wherein the means for elimination of interruptions include first means for storing a peak value of the first potential difference and second means for storing a second peak value of the second potential difference and means for finding of a mean value from the first and second peak value.

12. Apparatus according to claim 1, wherein the measurement electrode is designed as a touch electrode.

13. Apparatus according to claim 1, wherein the earth electrode is designed as a surface electrode.

14. Apparatus according to claim 1, wherein the measurement electrode or earth electrode are carbon electrodes.

15. Apparatus according to claim 14, wherein the carbon electrodes comprise synthetically bound carbon fibres.

16. Apparatus according to claim 1 further comprising means for digitalizing of measurement values and an interface for indication of measurement values on a personal computer.

17. Apparatus according to claim 1, wherein several measurement places are provided for measurement at different measure points.

18. Apparatus according to claim 1 further comprising a comparator for comparing amount of the first or second potential difference with a pre-set limit value, which sets evaluation of measurement values in motion, when the limit value is exceeded.

19. Apparatus according to claim 1 further comprising means for production of a time-phased stimulus current and a stimulus current electrode, for the production of a third electrical skin contact.

20. Apparatus according to claim 19, wherein strength of the stimulus current is adjustable.

* * * * *

UNITED STATES PATENT AND TRADEMARK OFFICE
CERTIFICATE OF CORRECTION

PATENT NO. : 6,295,468 B1
DATED : September 25, 2001
INVENTOR(S) : Hess

Page 1 of 1

It is certified that error appears in the above-identified patent and that said Letters Patent is hereby corrected as shown below:

<u>Title page,</u>
ABSTRACT,
Line 6, delete "earthling" and insert -- earthing --

<u>Column 12 claim 11,</u>
Line 25, insert the word -- first -- before the word "peak"

Signed and Sealed this

Ninth Day of April, 2002

Attest:

*Attesting Officer*

JAMES E. ROGAN
*Director of the United States Patent and Trademark Office*